(12) United States Patent
Gordon

(10) Patent No.: US 9,663,546 B2
(45) Date of Patent: May 30, 2017

(54) METAL AMIDES OF CYCLIC AMINES

(71) Applicant: President and Fellows of Harvard College, Cambridge, MA (US)

(72) Inventor: Roy Gerald Gordon, Cambridge, MA (US)

(73) Assignee: President and Fellows of Harvard College, Cambridge, MA (US)

(*) Notice: Subject to any disclaimer, the term of this patent is extended or adjusted under 35 U.S.C. 154(b) by 0 days.

(21) Appl. No.: 14/906,386

(22) PCT Filed: Jul. 25, 2014

(86) PCT No.: PCT/US2014/048220
§ 371 (c)(1),
(2) Date: Jan. 20, 2016

(87) PCT Pub. No.: WO2015/013630
PCT Pub. Date: Jan. 29, 2015

(65) Prior Publication Data
US 2016/0152649 A1 Jun. 2, 2016

Related U.S. Application Data

(60) Provisional application No. 61/858,873, filed on Jul. 26, 2013.

(51) Int. Cl.
*C07F 15/06* (2006.01)
*C07F 7/28* (2006.01)
(Continued)

(52) U.S. Cl.
CPC .......... *C07F 15/065* (2013.01); *C07D 207/46* (2013.01); *C07D 211/92* (2013.01);
(Continued)

(58) Field of Classification Search
CPC .... C07F 12/065; C07F 15/045; C07F 15/025; C07F 13/005; C07F 11/005; C07F 7/28; C07D 207/46; C07D 211/92
(Continued)

(56) References Cited

U.S. PATENT DOCUMENTS 4,929,733 A  5/1990  Hesse et al.
6,887,958 B1  5/2005  Mihan et al.
(Continued)

FOREIGN PATENT DOCUMENTS

EP  0423033 A1  4/1991

OTHER PUBLICATIONS

Couet et al., "Influence of the chemical structure of nitroxyl spin labels on their reduction by ascorbic acid," Tetrahedron, vol. 41, pp. 1165-1172 (1985).
(Continued)

*Primary Examiner* — Porfirio Nazario Gonzalez
(74) *Attorney, Agent, or Firm* — Wilmer Cutler Pickering Hale and Dorr LLP

(57) ABSTRACT

Compounds, and oligomers of the compounds, are synthesized with cyclic amine ligands attached to a metal atom. These compounds are useful for the synthesis of materials containing metals. Examples include pure metals, metal alloys, metal oxides, metal nitrides, metal phosphides, metal sulfides, metal selenides, metal tellurides, metal borides, metal carbides, metal silicides and metal germanides. Techniques for materials synthesis include vapor deposition (chemical vapor deposition and atomic layer deposition), liquid solution methods (sol-gel and precipitation) and solid-state pyrolysis. Suitable applications include electrical interconnects in microelectronics and magnetoresistant layers in magnetic information storage devices. The films have very uniform thickness and high step coverage in narrow holes.

38 Claims, 1 Drawing Sheet

(51) Int. Cl.
  *C07F 11/00* (2006.01)
  *C07F 13/00* (2006.01)
  *C07D 207/46* (2006.01)
  *C07D 211/92* (2006.01)
  *C07F 15/02* (2006.01)
  *C07F 15/04* (2006.01)
  *H01L 21/768* (2006.01)

(52) U.S. Cl.
  CPC .............. *C07F 7/28* (2013.01); *C07F 11/005* (2013.01); *C07F 13/005* (2013.01); *C07F 15/025* (2013.01); *C07F 15/045* (2013.01); *H01L 21/7685* (2013.01)

(58) Field of Classification Search
  USPC ................. 548/402; 546/11, 2; 427/255.7
  See application file for complete search history.

(56) References Cited

U.S. PATENT DOCUMENTS

| | | | |
|---|---|---|---|
| 7,514,119 B2 | 4/2009 | Ma et al. | |
| 7,919,638 B2 | 4/2011 | Lipiecki et al. | |
| 8,236,381 B2 | 8/2012 | Okubo | |
| 8,268,665 B2 | 9/2012 | Hunks et al. | |
| 2009/0124039 A1 | 5/2009 | Roeder et al. | |
| 2010/0034695 A1* | 2/2010 | Okubo | C23C 16/18 420/580 |

OTHER PUBLICATIONS

Gehrhus et al., "Synthesis and crystal structure of trimeric sodium 2,2,6,6-tetramethylpiperidide (NaTMP)," Journal of Organometallic Chemistry, vol. 587, pp. 88-92, (1999).

International Search Report and Written Opinion issued on Oct. 15, 2014, in international application PCT/US14/48220, filed Jul. 25, 2014, 14 pages.

Lunt, "Synthesis of Tetraalkylpyrrolidines From γ-Nitroketones," Nitro Compounds, Proc. Int. Symposium, Tetrahedron Suppl., vol. 20, Suppl. 1, 25 pages (1963).

McGeary et al., "Tantalum(I) Alkyne Complexes: $Ta(CO)_2(\eta^2\text{-}RC{\equiv}CR)(I)L_2$," Organometallics, vol. 7, No. 2, 11 pages (1988).

Stork et al., "Facile Synthesis of 3-Formyl-2,2,5,5-tetramethyl-1-oxypyrroline," Synthesis, No. 8, pp. 1309-1312, (1999).

* cited by examiner

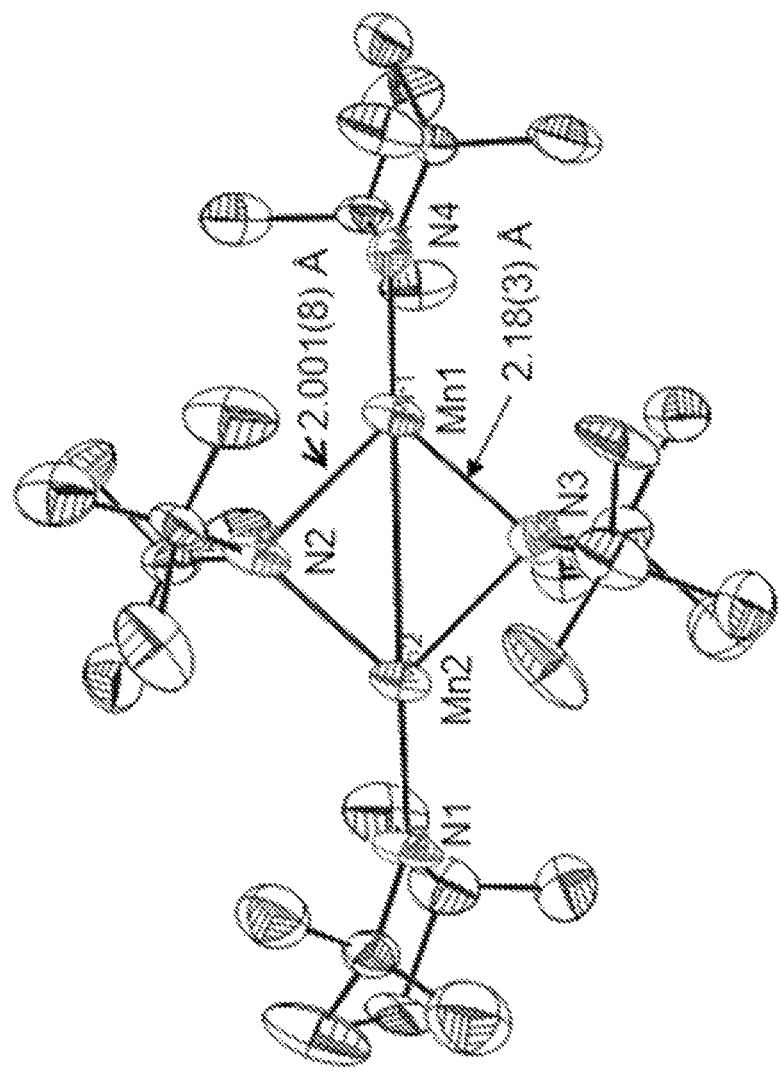

METAL AMIDES OF CYCLIC AMINES

CROSS-REFERENCES TO RELATED APPLICATIONS

This application is a U.S. National Stage application under 35 U.S.C. §371 of International Patent Application No. PCT/US14/48220, filed Jul. 25, 2014, which claims the benefit of the earlier filing date of U.S. Patent Application No. 61/858,873, filed on Jul. 26, 2013, the contents of which are hereby i-s-incorporated by reference in their entireties.

FIELD OF THE INVENTION

The present disclosure relates to novel materials which may be used for deposition of conformal films containing metals on solid substrates, and in particular, to films including chromium, manganese, iron, cobalt, nickel, or compounds including their oxides or nitrides. The present disclosure may be applied to the fabrication of microelectronic devices.

DESCRIPTION OF THE RELATED ART

As the speed and functionality of semiconductor microelectronic devices are improved, new materials and deposition processes are needed. The structures involved are smaller and increasingly three-dimensional. This trend is described in the International Technology Roadmap for Semiconductors, published on the Internet at http://www.itrs.net/Links/2013ITRS/Home2013.htm.

Widely-used techniques of physical vapor deposition (PVD), such as sputtering and evaporation, typically have poor step coverage, for example, giving only 20% thickness at the bottom of a hole with aspect ratio 5:1. Thus, there is an increasing need for techniques that can produce conformal coatings on three-dimensional structures.

One method that is suitable for making smooth, conformal layers is vapor deposition. One version of vapor deposition is called "atomic layer deposition", or ALD (also known as atomic layer epitaxy). The ALD process deposits thin layers of solid materials using two or more different vapor phase precursors. The surface of a substrate onto which film is to be deposited is exposed to a dose of vapor from one precursor. Then any excess unreacted vapor from that precursor is pumped away. Next, a vapor dose of the second precursor is brought to the surface and allowed to react. This cycle of steps can be repeated to build up thicker films. ALD reactions are self-limiting, so that only a certain maximum thickness can form in each cycle, after which no further deposition occurs during that cycle, even if excess reactant is available. Because of this self-limiting character, ALD reactions produce coatings with highly uniform thicknesses. Uniformity of ALD film thicknesses extends not only over flat substrate surfaces, but also into narrow holes and trenches. This ability of ALD to make conformal films is called "good step coverage."

Another version of vapor deposition is chemical vapor deposition (CVD). In a CVD process, a vapor or a vapor mixture reacts to deposit material on a surface. The reaction may be initiated by heating the surface, or by energy supplied electrically (plasma-activation), by light or other means. If the reactions on the surface are slow compared to the rate of transport up to the surface, then films with good conformality may also be obtained by CVD at higher deposition rates than those obtainable by ALD.

PVD methods are generally non-selective, in that they deposit on any surface. It is sometimes advantageous to selectively deposit on certain materials and not on others. For example, selective deposition of manganese or cobalt on top of copper, but not on adjacent insulators, can stabilize narrow copper lines against failure by electromigration. Some CVD and ALD techniques demonstrate selective deposition.

SUMMARY OF THE INVENTION

Precursors for vapor deposition of metals or metal-containing compounds are disclosed.

One aspect of the present disclosure includes metal amides with sterically demanding cyclic amine ligands. These compounds can be useful as precursors for vapor deposition. In one or more embodiments, the metal cyclic amine has the general formula $MA_x$ where x is selected to provide compound neutrality. Typically, x is 2 or 3. $MA_x$ is preferably a monomer, but may be an oligomer, in which case the compound may be reported as $[MA_x]_y$, where y is the degree of oligomerization and typically ranges up to 3 (trimer), more preferably 2 (dimer), and most preferably 1 (monomer). Additional neutral ligands L may also be present, corresponding to a formula $(MA_xL_n)_y$, where n is a positive number.

One preferred class of compounds comprises metal pyrrolidinates having the formula

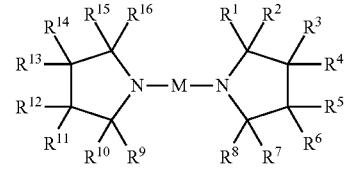

or oligomers thereof where the R" are chosen independently from hydrogen, alkyl, substituted alkyl, cycloalkyl, substituted cycloalkyl, aryl, substituted aryl, alkenyl, substituted alkenyl, alkynyl, substituted alkynyl, trialkylsilyl, dialkylamide or haloalkyl groups, wherein the haloalkyl groups include fluoroalkyls, chloroalkyls and bromoalkyls.

Another preferred class of compounds comprises metal piperidinates having the formula

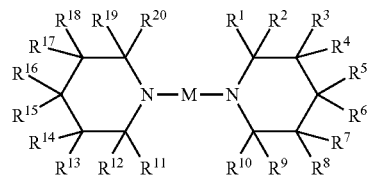

or oligomers thereof where the R" are chosen independently from hydrogen, alkyl, substituted alkyl, cycloalkyl, substituted cycloalkyl, aryl, substituted aryl, alkenyl, substituted alkenyl, alkynyl, substituted alkynyl, trialkylsilyl, dialkylamide or haloalkyl groups, wherein the haloalkyl groups include fluoroalkyls, chloroalkyls and bromoalkyls.

Also contemplated are compounds with mixed ligands of these types:

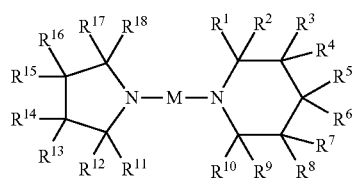

or oligomers thereof where the R″ are chosen independently from hydrogen, alkyl, substituted alkyl, cycloalkyl, substituted cycloalkyl, aryl, substituted aryl, alkenyl, substituted alkenyl, alkynyl, substituted alkynyl, trialkylsilyl, dialkylamide or haloalkyl groups, wherein the haloalkyl groups include fluoroalkyls, chloroalkyls and bromoalkyls.

Yet another class of compounds comprises metal pyrrolidinates having the formula

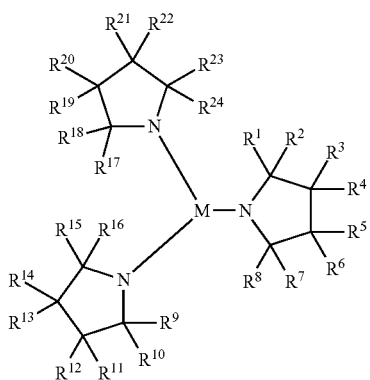

or oligomers thereof or oligomers thereof where "R‴" where n may be any integer between 1 and 24, may be chosen independently from hydrogen, alkyl, substituted alkyl, cycloalkyl, substituted cycloalkyl, aryl, substituted aryl, alkenyl, substituted alkenyl, alkynyl, substituted alkynyl, trialkylsilyl, dialkylamide or haloalkyl groups, wherein the haloalkyl groups include fluoroalkyls, chloroalkyls and bromoalkyls.

Also, included are the class of compounds comprising metal piperidinate having the formula

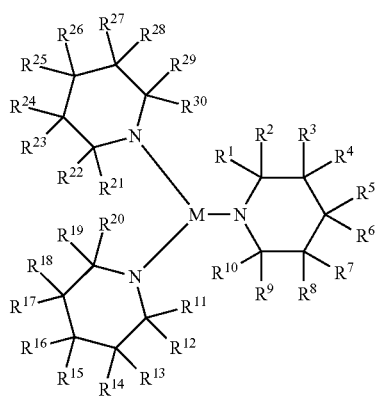

or oligomers thereof where "R‴" where n may be any integer between 1 and 30, may be chosen independently from hydrogen, alkyl, substituted alkyl, cycloalkyl, substituted cycloalkyl, aryl, substituted aryl, alkenyl, substituted alkenyl, alkynyl, substituted alkynyl, trialkylsilyl, dialkylamide or haloalkyl groups, wherein the haloalkyl groups include fluoroalkyls, chloroalkyls and bromoalkyls.

In yet another aspect of the embodiment, also envisaged are compounds with three ligands, wherein at least one ligand is pyrrolidinate and at least one is a piperidinate.

In one embodiment, metal compounds with cyclic amine ligands provide greater thermal stability than metal non-cyclic amides.

Another aspect of the present disclosure includes a process for depositing uniform, conformal and smooth films comprising metals such as chromium, manganese, iron, cobalt, nickel, zinc and magnesium.

Metal-containing coatings can be deposited according to the invention at relatively low temperatures, and without plasma damage to substrates.

In one embodiment, metal-containing coatings with extremely uniform thicknesses are formed. In another embodiment, coatings may be formed selectively on certain surfaces while not depositing on other surfaces.

A related aspect of the present disclosure is the deposition of metal-containing coatings under conditions that produce good adhesion between substrates and the deposited coating, and for example, adhere strongly to oxide substrates.

The process permits deposition of metal-containing coatings with extremely smooth surfaces.

The process also provides vapor deposition of highly uniform metal-containing coatings over a range of conditions such as concentrations of reactants and position of the substrate inside the reactor.

In other aspects, conformal metal-containing coatings are formed over substrates with narrow holes, trenches or other structures. This ability is commonly known as "good step coverage." The coatings may be substantially free of pinholes or other mechanical defects.

In one aspect, vapors of a volatile cyclic amide are reacted with hydrogen gas or other reducing reagents at a surface to produce thin layers of metal on the surface.

In another aspect, vapors of a volatile cyclic amide are reacted with ammonia gas or other nitrogen source at a surface to produce thin layers of a metal nitride on the surface. Examples of this reaction include reacting manganese(II) cyclic amides with ammonia to deposit manganese nitride.

In yet another aspect, vapors of a volatile cyclic amide are reacted with water vapor or other oxygen source at a surface to produce thin layers of a metal oxide on the surface. Examples of this reaction include reacting magnesium cyclic amides with water vapor to deposit magnesium oxide.

In a further aspect, vapors of a volatile cyclic amide are reacted with a tris-alkoxysilanol vapor or other silanol sources at a surface to produce thin layers of a metal silicate on the surface. Examples of this reaction include reacting manganese(II) cyclic amides with tris-tert-pentoxysilanol to deposit manganese silicate.

In other embodiments, cyclic amides of manganese, iron, cobalt, nickel, zinc, chromium, vanadium, titanium, magnesium, calcium, strontium, barium, tellurium, cadmium, tin, lead, palladium, platinum, rhodium, ruthenium, osmium, iridium, molybdenum, tungsten, niobium, tantalum, aluminum, gallium, scandium, antimony, indium, lutetium, ytterbium, thulium, erbium, thallium, yttrium, holmium, dysprosium, terbium, gadolinium, europium, samarium, neodymium, praseodymium, cerium, bismuth, and uranium are used as for vapor deposition of thin films comprising one or more of these metals.

In other embodiments, the deposited metal-containing coatings possess high electrical conductivity or other useful properties.

In other embodiments, the compound can be dissolved in a solvent such as a hydrocarbon and the resulting solution is used for deposition. Suitable hydrocarbons include alkanes, alkenes, terpenes or their combinations thereof. Specifically, dodecane, tetradecane, 2,6,10-trimethyldodecane, 2,2,4,4,6,8,8-heptamethylnonane, 2,6,10-trimethylpentadecane and 2,6,10,14-tetramethylpentadecane or combinations thereof can be used as solvents for dissolving these compounds.

In other embodiments, the compound can be dissolved in a solvent, such as trialkylamine, and the resulting solution can be used for deposition. Suitable trialkylamines that can be used for dissolving these compounds include tri-n-butylamine, tri-n-pentylamine, tri-n-hexylamine, tri-n-heptylamine, tri-n-octylamine or combinations thereof.

The coatings may be used as connectors in micro-electronic devices, e.g., as manganese-containing adhesion/barrier layers for copper films in micro-electronic interconnect structures. Coatings may also be placed on powders, wires or around and within complicated mechanical structures.

BRIEF DESCRIPTION OF THE DRAWINGS

The foregoing and various other aspects, features, and advantages of the present invention, as well as the invention itself, may be more fully appreciated with reference to the following detailed description of the invention when considered in connection with the following drawings. The drawings are presented for the purpose of illustration only and are not intended to be limiting of the invention, in which:

The FIGURE is a diagram of the structure of bis(2,2,5,5-tetramethylpyrrolidino)manganese(II) dimer molecules in their crystal, as determined by the methods of X-ray crystallography.

DETAILED DESCRIPTION OF THE INVENTION

"Metal cyclic amides," as used herein, are compounds that include a metal or metals attached to anionic ligands derived from cyclic amines. A "cyclic amine," as used herein, means a heterocyclic compound whose ring structure includes one nitrogen atom while the other ring atoms (typically 4 or 5) are carbon.

In one or more embodiments, the metal cyclic amine has the general formula $MA_x$ where x is selected to provide compound neutrality. Typically, x is 2 or 3. $MA_x$ is preferably a monomer, but may be an oligomer, in which case the compound may be reported as $[MA_x]_y$, where y is the degree of oligiomerization and typically ranges up to 3 (trimer), more preferably 2 (dimer), and most preferably 1 (monomer). Additional neutral ligands L may also be present, corresponding to a formula $(MA_xL_n)_y$, where n is a positive number.

In one or more embodiments, M is a main group element, transition metal or rare earth metal in an oxidation state typically 2 or 3. Exemplary metals include manganese, iron, cobalt, nickel, zinc, chromium, vanadium, titanium, magnesium, calcium, strontium, barium, tellurium, cadmium, tin, lead, palladium, platinum, rhodium, ruthenium, osmium, iridium, molybdenum, tungsten, niobium, tantalum, aluminum, gallium, scandium, antimony, indium, lutetium, ytterbium, thulium, erbium, thallium, yttrium, holmium, dysprosium, terbium, gadolinium, europium, samarium, neodymium, praseodymium, cerium, bismuth, and uranium.

In one embodiment, cyclic amines have five-member pyrrolidinate rings and are represented by the following structure or oligomers thereof when forming compounds with metals M in the oxidation state +2:

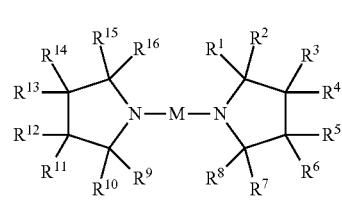

1

In this formula, $R^1$ through $R^{16}$, or "R'''" where n=1-16, represent groups made from one or more non-metal atoms. In some embodiments, R'' may be chosen independently from hydrogen, alkyl, substituted alkyl, cycloalkyl, substituted cycloalkyl, aryl, substituted aryl, alkenyl, substituted alkenyl, alkynyl, substituted alkynyl, trialkylsilyl, dialkylamide or haloalkyl groups, wherein the haloalkyl groups include fluoroalkyls, chloroalkyls and bromoalkyls. In some embodiments, the groups attached to carbons adjacent to nitrogen (that is, $R^1$, $R^2$, $R^7$, $R^8$, $R^9$, $R^{10}$, $R^{15}$ and $R^{16}$) are not hydrogen, so that the steric bulk of the cyclic amine ligands provides monomeric compounds, which are more volatile than oligomeric compounds. In certain embodiments, the cyclic amine ligands are 2,2,5,5-tetramethylpyrrolidinates forming compounds with metals M in the oxidation state +2:

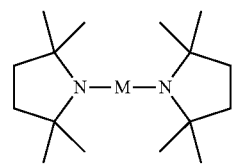

2

In one or more embodiments, the cyclic amine ligands are substituted piperidinates, forming compounds with metals M in the oxidation state +2 represented by the following structure or oligomers thereof:

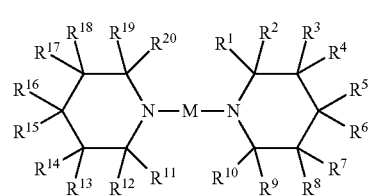

3

In this formula, $R^1$ through $R^{20}$, or "R'''" where n=1-20, represent groups made from one or more non-metal atoms. In some embodiments, R'' may be chosen independently from hydrogen, alkyl, substituted alkyl, cycloalkyl, substituted cycloalkyl, aryl, substituted aryl, alkenyl, substituted alkenyl, alkynyl, substituted alkynyl, trialkylsilyl, dialkylamide or haloalkyl groups, wherein the haloalkyl groups include fluoroalkyls, chloroalkyls and bromoalkyls. In preferred embodiments, the groups attached to carbons adjacent to nitrogen (that is, $R^1$, $R^2$, $R^9$, $R^{10}$, $R^{11}$, $R^{12}$, $R^{19}$ and $R^{20}$) are not hydrogen, so that the steric bulk of the ligands provides monomeric compounds, which are more volatile than oligomeric compounds.

In some embodiments, the cyclic amine ligands are 2,2,6,6-tetramethylpiperidinates forming compounds with metals M in the oxidation state +2:

4

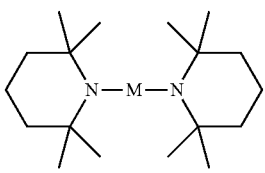

Some suitable metals in the +2 oxidation state include Mn(II), Fe(II), Co(II), Ni(II), Zn(II), Cr(II), V(II), Ti(II), Cu(II), Ca(II), Sr(II), Ba(II), Te(II), Pb(II), Pd(II), Pt(II), Rh(II), Ru(II) or Os(II).

In certain embodiments, the cyclic amines are tris(pyrrolidinate) forming compounds with M in the oxidation state +3 represented by the following structure or oligomers thereof

5

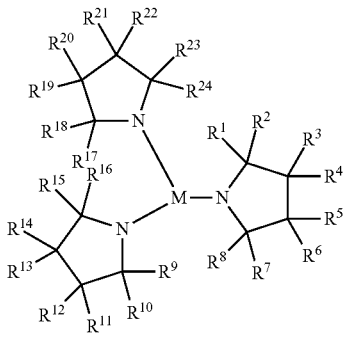

In formula 5, "$R^{n}$", where n is any integer between 1 and 24, represent groups chosen independently from hydrogen, alkyl, substituted alkyl, cycloalkyl, substituted cycloalkyl, aryl, substituted aryl, alkenyl, substituted alkenyl, alkynyl, substituted alkynyl, trialkylsilyl, dialkylamide or haloalkyl groups, wherein the haloalkyl groups include fluoroalkyls, chloroalkyls and bromoalkyls.

Some suitable metals in the +3+ oxidation state in formula 5 include aluminum, cobalt, iron, gallium, vanadium, titanium, rhodium, ruthenium, osmium, iridium, chromium, molybdenum, tungsten, niobium, tantalum, scandium, antimony, indium, lutetium, ytterbium, thulium, erbium, thallium, yttrium, holmium, dysprosium, terbium, gadolinium, europium, samarium, neodymium, praseodymium, cerium, bismuth or uranium.

In certain embodiments, the cyclic amines are tris(piperidinate) forming compounds with M in the oxidation state +3 represented by the following structure or oligomers thereof:

6

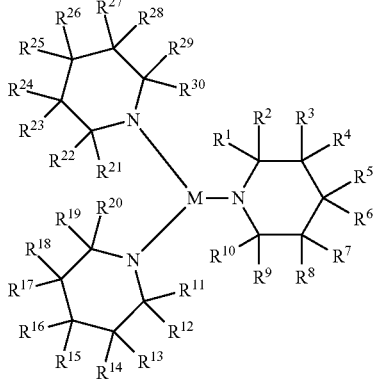

In formula 6, "$R^{n}$", where n is any integer between 1 and 30, represent groups chosen independently from hydrogen, alkyl, substituted alkyl, cycloalkyl, substituted cycloalkyl, aryl, substituted aryl, alkenyl, substituted alkenyl, alkynyl, substituted alkynyl, trialkylsilyl, dialkylamide or haloalkyl groups, wherein the haloalkyl groups include fluoroalkyls, chloroalkyls and bromoalkyls.

Some suitable metals in the +3+ oxidation state in formula 6 include aluminum, cobalt, iron, gallium, vanadium, titanium, rhodium, ruthenium, osmium, iridium, chromium, molybdenum, tungsten, niobium, tantalum, scandium, antimony, indium, lutetium, ytterbium, thulium, erbium, thallium, yttrium, holmium, dysprosium, terbium, gadolinium, europium, samarium, neodymium, praseodymium, cerium, bismuth or uranium.

Synthetic Scheme

In certain embodiments, cyclic amines and their compounds with metals described herein can be synthesized according to the reactions described in the examples. Adding different substituents to the cyclic amines can be accomplished by the selection of different organic starting materials as is understood by one of skill in the art.

Vapor Deposition

In a vapor deposition process, the metal cyclic amine vapor and, optionally, a vapor of a second reactant are supplied to a surface. When the vapors are supplied at the same time to a surface, or if the optional second reactant is omitted, the process is called chemical vapor deposition (CVD). When the vapors are supplied alternately to a surface, then the process is called atomic layer deposition (ALD). Typical second reactants include hydrogen gas, ammonia gas, water, oxygen, hydrogen peroxide, nitrogen dioxide, ozone, hydrogen sulfide, diborane. When hydrogen gas or another reducing gas is chosen as the second reactant, a metal may be deposited. When ammonia gas or another reactive source of nitrogen is chosen as the second reactant, a metal nitride is deposited. When water vapor, oxygen or ozone or another reactive source of oxygen is chosen as the second reactant, a metal oxide is deposited. When hydrogen sulfide or another reactive source of sulfur is chosen as the second reactant, a metal sulfide is deposited. When diborane or another reactive source of boron is chosen as the second reactant, a metal boride is deposited.

According to one or more embodiments, a metal cyclic amide is introduced onto a substrate as a vapor. Vapors of precursors may be formed by conventional methods from either liquid or solid precursors. In one or more embodiments, a liquid precursor or a liquid solution of it may be vaporized by flowing it along a tube heated, for example to about 100 to 200° C. A carrier gas may also be flowed through the heated tube to assist in the transport of the vapor into the deposition region. The liquid may also be vaporized by nebulization into a carrier gas preheated above the vaporization temperature. The nebulization may be carried out pneumatically, ultrasonically, or by other suitable methods. Solid precursors to be nebulized may be dissolved in organic solvents, including hydrocarbons such as decane, dodecane, tetradecane, toluene, xylene and mesitylene, ethers, esters, ketones, amines and chlorinated hydrocarbons. Solutions of liquid precursors may have lower viscosities than pure liquid precursors, so that in some cases it may be preferable to nebulize and evaporate solutions rather than pure liquids. The precursor liquid or precursor solutions may also be evaporated with thin-film evaporators, by direct injection of the liquids or solutions into a heated zone, or by heating in a bubbler. Commercial equipment for vaporization of liquids is made by Brooks Instruments (Hatfield, Pa.), MKS Instruments (Andover, Mass.), ATMI, Inc. (Danbury, Conn.) and COVA Technologies (Colorado Springs, Colo.). Ultrasonic nebulizers are made by Sonotek Corporation (Milton, N.Y.) and Cetac Technologies (Omaha, Nebr.).

The metal precursors described herein may be reacted with a reducing agent, e.g., hydrogen gas, to form films of the metal. For example, a nickel(II) cyclic amine may be reacted with hydrogen gas to form nickel metal. In other embodiments, the metal precursors of the present invention may also be reacted with other suitably reactive reducing compounds to form metals. In some embodiments, the metal precursors described herein may be reacted with ammonia gas to form metal nitrides. For example, a cobalt(II) cyclic amine may be reacted with ammonia gas to form cobalt nitride. In other embodiments, the metal precursors described herein may be reacted with water vapor to form metal oxides. For example, a nickel(II) cyclic amine may be reacted with water vapor to form nickel oxide.

Deposition of the precursors described herein may be carried out using atomic layer deposition (ALD). ALD introduces a metered amount of a first reactant into a deposition chamber having a substrate therein for layer deposition. A thin layer of the first reactant is deposited on the substrate. Then any unreacted first reactant and volatile reaction by-products are removed by a vacuum pump and, optionally, a flow of inert carrier gas. A metered amount of a second reactant component is then introduced into the deposition chamber. The second reactant deposits on and reacts with the already deposited layer from the first reactant. Alternating doses of first and second reactants are introduced into the deposition chamber and deposited on the substrate to form a layer of controlled composition and thickness. The time between doses may be on the order of seconds and is selected to provide adequate time for the just-introduced component to react with the surface of the film and for any excess vapor and byproducts to be removed from the headspace above the substrate. It has been determined that the surface reactions are self-limiting so that a reproducible layer of predictable composition is deposited. As will be appreciated by one of ordinary skill in the art, deposition processes utilizing more than two reactant components are within the scope of the invention.

In other embodiments, deposition of the precursors described herein may be carried out by CVD.

EXAMPLES

The following examples are provided for the purpose of illustration only and should not be construed as limiting the invention in any manner.

All reactions and manipulations described in these methods can be conducted under a pure nitrogen atmosphere using either an inert atmosphere box or standard Schlenk techniques. The compounds produced by these procedures generally react with moisture and/or oxygen in the ambient air, and hence, can be stored and handled under an inert, dry atmosphere such as pure nitrogen or argon gas.

Example 1. Synthesis of 2,2,5,5-tetramethylpyrrolidine by ring contraction

The following sequence of reactions can also be used to prepare 2,2,5,5-tetramethylpyrrolidine:

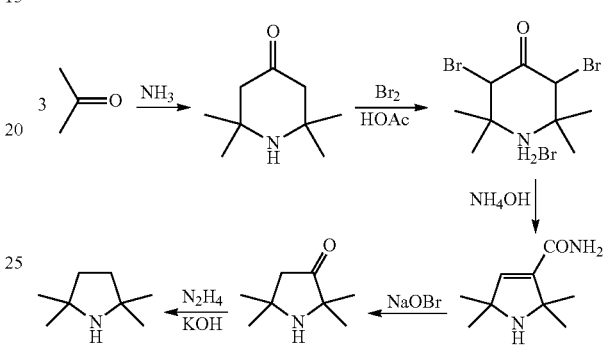

These steps are described in more detail as follows:

Condensation of acetone with ammonia to form 2,2,6,6-tetramethylpiperidin-4-one:

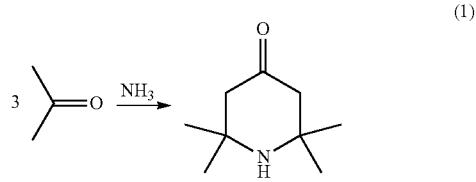

(1)

This intermediate, 2,2,6,6-tetramethylpiperidin-4-one, can also be purchased commercially.

Bromination of 2,2,6,6-tetramethylpiperidin-4-one:

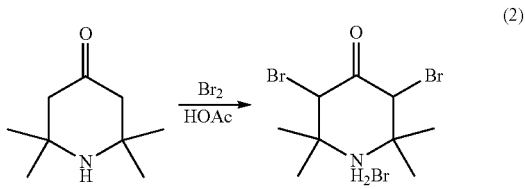

(2)

2,2,6,6-Tetramethylpiperidin-4-one (100 g, 0.644 mol) was dissolved in glacial acetic acid (HOAc) (395 mL) under water bath cooling. A solution of $Br_2$ (205.8 g, 1.288 mol) in HOAc (285 mL) was added dropwise over the course of 6 hours. After 1 day, the reaction mixture was filtered. The isolated solid was washed with HOAc (200 mL), $H_2O$ (200 mL) and finally with $Et_2O$ (2×200 mL). After air-drying for 7-10 days the product was obtained as a light beige powder (229.55 g, 90%). mp 201° C. (dec.). $^1H$ NMR ($CDCl_3$/ MeOH-$d_4$, 2:1 v/v): 1.45 (s, 6H, 2 $CH_3$), 1.88 (s, 6H, 2 $CH_3$), 5.63 (s, 2H, 2 CHBr). See S. W. Stork and M. W. Makinen, "Facile Synthesis of 3-Formyl-2,2,5,5-tetramethyl-1-oxypyrroline," Synthesis 1309 (1999).

Ring contraction by Favorskii rearrangement in ammonia:

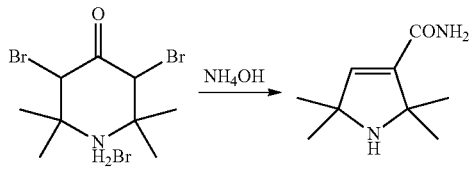

(3)

3,5-Dibromo-2,2,6,6-tetramethylpiperidin-4-one (75 g, 0.19 mol) was added in small portions to 750 mL of concentrated aqueous ammonia with magnetic stirring. After several minutes the salt dissolved. The solution was saturated with sodium hydroxide added in the form of tablets. A light, needle-shaped precipitate formed. After filtration and drying, 25 g (78%) of a white solid was obtained with sufficient purity to be used in the next step. See C. Sandris and G. Ourisson, Bull. Soc. Chim. France 345 (1958); H. Pauly, Ann. Chem. 322, 77 (1902).

Hofmann degradation of the carboxamide to the pyrrolidone:

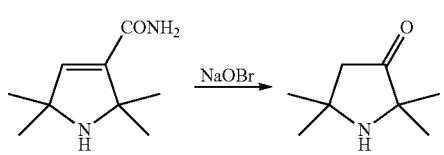

(4)

A solution of sodium hypobromite was prepared by dissolving 43 g of sodium hydroxide in 150 mL of distilled water, cooling to 0° C. in an ice bath, and slowly adding 35 g of bromine while stirring vigorously. After about 10 minutes, a solution of 30 g of 3-aminocarbonyl-2,2,6,6-tetramethyl-3-pyrroline in 250 mL of distilled water was added gradually to the cooled and stirred solution of sodium hypobromite. The initially colorless or slightly yellowish reaction mixture was gradually heated to reflux on a water bath. Its color became greenish, then yellow, orange and finally dark red after about an hour. As soon as it turned dark red, the solution was cooled to room temperature. 150 g of sodium hydroxide pellets were added with stirring. As soon as the pellets dissolved, the mixture was immediately steam-distilled into a receiving flask cooled in ice, until about 150 mL of distillate was obtained. This distillate was saturated with sodium hydroxide and sodium chloride, and then extracted with ether. After low-pressure distillation (80° C./40 Torr), 13.2 g (55%) of a colorless liquid was obtained. (b.p. 169° C./747 Torr). See C. Salvi, C. Fabre, A. Rassat, R. Chiarelli, European Patent Application 423 033 (1990); R. M. Dupeyre, A. Rassat and P. Rey, Bull. Soc. Chim. France 3643 (1965); C. Sandris and G. Ourisson, Bull. Soc. Chim. France 345 (1958); H. Pauly, Ann. Chem. 322, 77 (1902).

Wolff-Kishner reduction of the ketone using hydrazine:

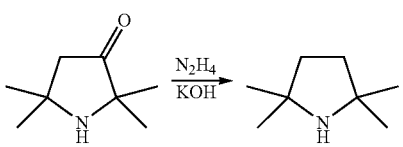

(5)

A mixture of 2,2,5,5-tetramethyl-3-oxopyrrolidine (1.97 g, 0.014 mol), hydrazine hydrate (2.1 ml, 0.042 mol), potassium hydroxide (2.8 g, 0.050 mol) and diethylene glycol monoethyl ether (10 mL) was heated at 135° C. until the evolution of nitrogen ceased (14 hr). The reflux condenser was then replaced with a distillation condenser and the bath temperature gradually increased to 195° C. The distillate was saturated with anhydrous potassium carbonate, and the organic layer separated and distilled at atmospheric pressure, collecting a fraction boiling at 105-125° C. This material was redistilled to give 1.3 g (73%) of pure 2,2,5,5-tetramethylpyrrolidine, b. p. 110-115° C. See W. R. Couet, R. C. Brasch, G. Sosnovsky, J. Lukszo, I. Prakash, C. T. Gnewuch and T. N. Tozer, "Influence of the chemical structure of nitroxyl spin labels on their reduction by ascorbic acid," Tetrahedron 41, 1165-1172 (1985).

Example 2. Synthesis of 2,2,5,5-tetramethylpyrrolidine from nitro ketones

The following reactions can be used to synthesize 2,2,5,5-tetramethylpyrrolidine from but-3-en-2-one and 2-nitropropane:

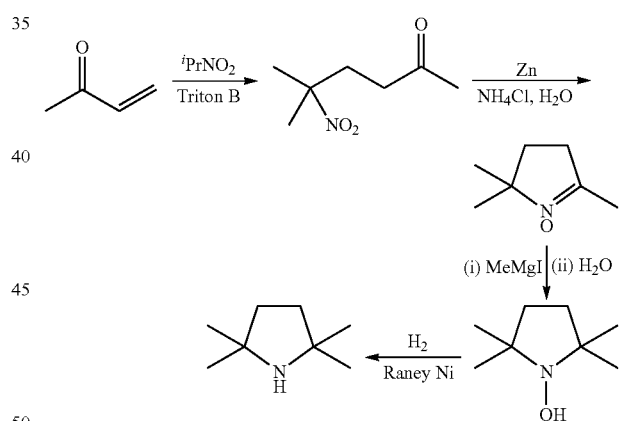

See E. Lunt, *Nitro Compounds, Proc. Int. Symposium, Tetrahedron Suppl.*, 291 (1963).

Example 3. Synthesis of 2,2,5,5-tetramethylpyrrolidine by catalytic cyclization 2,5-dimethyl-1,5-hexadiene is heated in the presence of a solid catalyst, such as a zeolite.

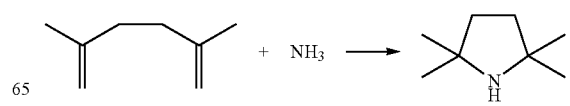

This synthesis could be scaled up industrially to run as a continuous process, but the yield and purity of the product are low. See Michael Hess, Wolfgang Hoelderich and Matthias Schwartzmann, Preparation of N-Heterocycles. U.S. Pat. No. 4,929,733(1990).

Example 4. Preparation of bis(2,2,5,5-tetramethylpyrrolidinato)manganese(II) dimer

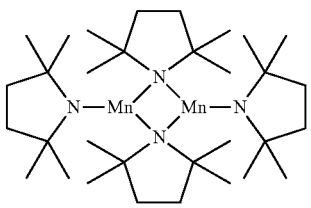

2,2,5,5-tetramethylpyrrolidine made according to Examples 1, 2 or 3 was reacted with n-butyl lithium in ether to produce lithium 2,2,5,5-tetramethylpyrrolidinate. The ether was evaporated under low pressure. $MnBr_2(THF)_2$ and pentane were added to the lithium 2,2,5,5-tetramethylpyrrolidinate. The reaction mixture was allowed to stir at room temperature until reaction was complete (typically overnight), and then was filtered to remove solid lithium bromide byproduct. The volatile solvents (pentane and tetrahydrofuran) were removed from the filtered liquid under vacuum, the flask being kept at room temperature by immersion in a water bath. The resulting crude bis(2,2,5,5-tetramethylpyrrolidinato)manganese(II) was then purified by vacuum sublimation at temperatures up to 80 C and collected on a water-cooled cold finger as a yellow solid. A study of the solid by X-ray crystallography showed that it is a dimer in the solid, as shown in the FIGURE and drawn in the formula above this paragraph.

Example 5. Preparation of bis(2,2,5,5-tetramethylpyrrolidinato)iron(II)

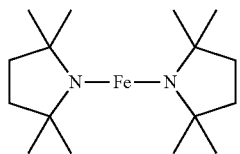

Example 4 is repeated with $FeBr_2(DME)$ in place of $MnBr_2(THF)_2$.

Example 6. Preparation of bis(2,2,5,5-tetramethylpyrrolidinato)cobalt(II)

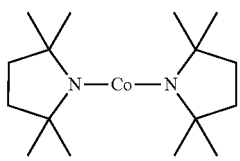

Example 4 is repeated with $CoBr_2(DME)$ in place of $MnBr_2(THF)_2$.

Example 7. Preparation of bis(2,2,5,5-tetramethylpyrrolidinato)nickel(II)

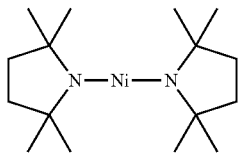

Example 4 is repeated with $NiBr_2(DME)$ in place of $MnBr_2(THF)_2$.

Example 8. Preparation of bis(2,2,6,6-tetramethylpiperidinato)manganese(II)

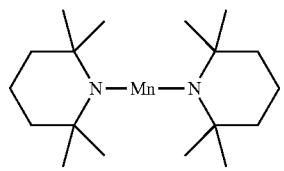

Commercially available 2,2,6,6-tetramethylpiperidine was reacted with n-butyl lithium in ether to form lithium 2,2,6,6-tetramethylpiperidinate. The ether was evaporated under vacuum. $MnBr_2(THF)_2$ and pentane were added to the lithium 2,2,6,6-tetramethylpiperidinate. The reaction mixture was allowed to stir at room temperature until reaction was complete (usually overnight), and then filtered to remove solid lithium bromide. The volatile solvents (pentane and tetrahydrofuran) were removed under vacuum, the flask being kept at room temperature by immersion in a water bath. The resulting crude bis(2,2,6,6-tetramethylpiperidinato)manganese(II) was purified by sublimation at a temperature up to 80 C and collected on a water-cooled cold finger as a yellow solid. X-ray analysis of the solid showed unit cell parameters a=11.17, b=15.08, c=16.28, $\alpha$=97.87, $\beta$=96.86, $\gamma$=105.61. These parameters have not been reported previously, showing that this is a new compound. However, the quality of the crystal was not sufficient to determine its molecular structure. Proton NMR has 3 or 4 broad resonances, showing that the compound is paramagnetic.

Example 9. Preparation of bis(2,2,6,6-tetramethylpiperidinato)iron(II)

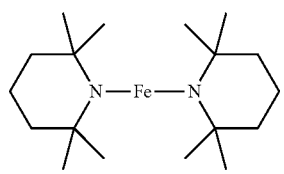

Example 8 is repeated with $FeI_2$ in place of $MnBr_2(THF)_2$.

Example 10. Preparation of bis(2,2,6,6-tetramethylpiperidinato)cobalt(II)

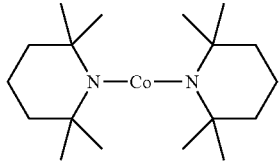

Example 8 is repeated with $CoBr_2(DME)$ in place of $MnBr_2(THF)_2$.

Example 11. Preparation of bis(2,2,6,6-tetramethylpiperidinato)nickel(II)

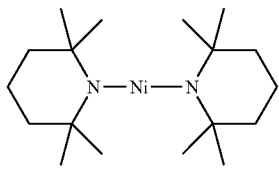

Example 8 is repeated with $NiBr_2(DME)$ in place of $MnBr_2(THF)_2$.

Example 12. Alternative preparation of bis(2,2,6,6-tetramethylpiperidinato)manganese(II), Mn(TMPP)$_2$

12a. Synthesis of n-butylsodium, nBuNa

The compound nBuNa was prepared following a literature procedure from *Organometallics* 1988, 7, 277. NaO$^t$Bu was made fresh from HO$^t$Bu and Na$^0$. Freshly prepared Na$^0$ foil was added to 2-4 fold excess HO$^t$Bu and stirred at reflux for 24 hours. The remaining HO$^t$Bu was removed in vacuum resulting in white solid NaO$^t$Bu that was immediately used in the synthesis of nBuNa.

12b. Synthesis of (2,2,6,6-tetramethylpiperidinato)sodium trimer, Na$_3$(TMPP)$_3$ The compound Na$_3$TMPP$_3$ was prepared following a literature procedure from *J. Organomet. Chem.* 1999, 587, 88. In some cases, adding excess nBuNa was necessary to ensure complete formation of Na$_3$TMPP$_3$. Incomplete conversion to Na$_3$TMPP$_3$ was determined by $^1$H NMR, which showed the presence of free TMPPH. $^1$H NMR (benzene-d$_6$, 500 MHz, δppm): 1.11 (br, 12H, CH$_3$), 1.36 (br, 4H, β-CH$_2$), 1.89 (br, 2H, γ-CH$_2$).

12c. Synthesis of bis(2,2,6,6-tetramethylpiperidinato)manganese(II), Mn(TMPP)$_2$ Crushed anhydrous beads of MnCl$_2$ (175 mg, 1.4 mmol) was refluxed for 18 hours in 10 mL of THF. Na$_3$TMPP$_3$ was prepared in 10 mL of hexanes as described previously (nBuNa (223 mg, 2.8 mmol); TMPPH (390 mg, 2.8 mmol); *J. Organomet. Chem.* 1999, 587, 88.) The freshly prepared Na$_3$TMPP$_3$ was added to the suspension of MnCl$_2$(THF) in cold THF (−35° C.). The reaction was allowed to warm to room temperature and stirred for 12 hours, yielding an orange-brown solution. The volatiles were removed in vacuum; the resulting oil was dissolved in hexanes (20 mL) and filtered through Celite to remove NaCl. The solvents were removed in vacuum yielding an orange-brown oil in 84% yield. $^1$H NMR shows 3 or 4 broad paramagnetic resonances that shift their positions between 0 and 20 ppm depending on the concentration. One representative $^1$H NMR (benzene-d$_6$, 500 MHz, δppm): 10.84, 8.86, 4.93, 3.54. Yellow crystals were grown from hexanes (unit cell: a=11.17, b=15.08, c=16.28, α=97.87, β=96.86, γ=105.61).

Example 13. Preparation of bis(2,2,6,6-tetramethylpiperidinato)titanium(II)

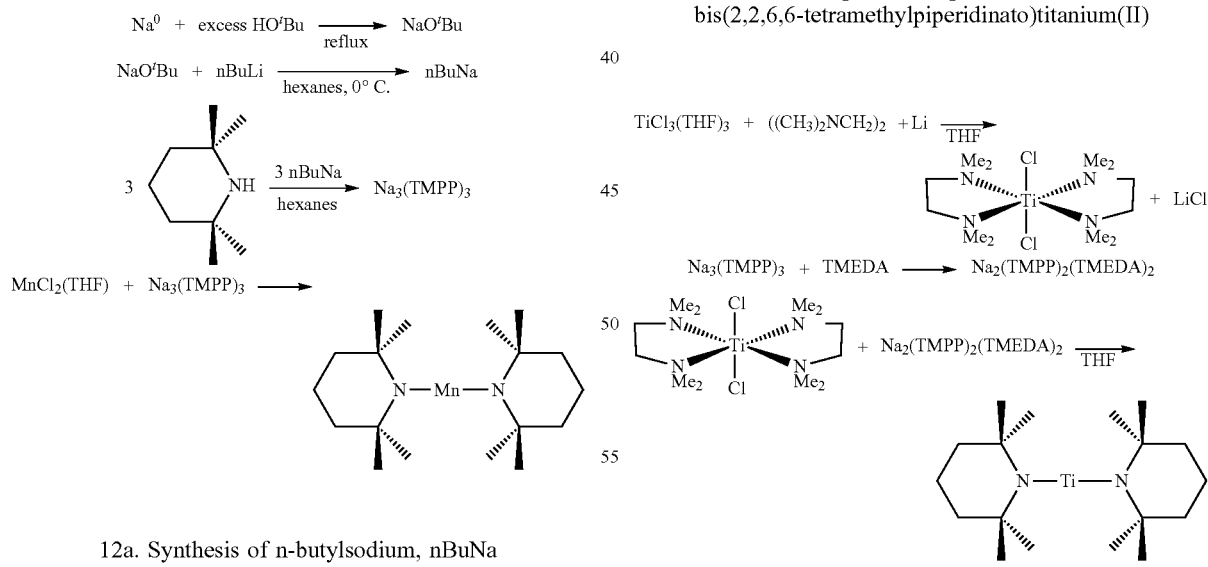

13a. Synthesis of Titanium Dichloride Complex with Tetramethylethylenediamine, TiCl$_2$(TMEDA)$_2$ TiCl$_2$(TMEDA)$_2$ was prepared using a synthesis adapted from a report in *Inorganic Chemistry* 1991, vol. 30, page 154. In an Ar glovebox, TMEDA (29 g, 0.25 mol) was added to a suspension of commercial (Sigma-Aldrich) TiCl$_3$(THF)$_3$ (15 g, 0.040 mol) in THF (100 mL) at −35° C. Very thin (paper thickness), freshly hammered lithium metal foil (0.95 g, 0.14 mol) was rinsed with hexanes, prior to adding the solid chunks to the reaction at −35° C. The reaction was allowed to warm to room temperature at which point a color change occurred from a green solution to a black/brown suspension. The reaction was vigorously stirred at room temperature for no more than 24 hours, but at least overnight. A solution of TMEDA (5 mL) and THF (170 mL) was cooled to −35° C. The reaction and filter apparatus were cooled in the cold well of the glovebox at −78° C. The cold TMEDA/THF solution was added to the cold reaction and immediately filtered through Celite (cold filtration) to remove the unreacted lithium metal. The solute was transferred to a cold Schlenk flask and concentrated to a final volume of 200 mL. The schlenk flask should remain in the cold well (at −78° C.) during the concentration process. During this time, a purple precipitate should begin to form. The resulting solution was stored at −35° C. for at least 24 hours, yielding a purple precipitate that was isolated by filtration. The purple crystals were washed with 20 mL of cold (−35° C.) THF. While TiCl$_2$(TMEDA)$_2$ is stable at room temperature when isolated as a solid, it was stored in a −35° C. freezer. Isolated yield: 45%. It is imperative that the reaction is kept cold during the entire workup. In all steps, glassware and solvent should be allowed to cool for at least 1 hour to ensure the appropriate temperature has been reached. Failure to rigorously cool apparatus and solvent will result in decomposition and lower yields.

13b. Synthesis of the dimer of (2,2,6,6-tetramethylpiperidinato)sodium complex with tetramethylethylenediamine, Na$_2$(TMPP)$_2$(TMEDA)$_2$ The compound Na$_2$(TMPP)$_2$(TMEDA)$_2$ was prepared following a literature procedure from *Chem. Eur. J.* 2008, 14, 8025. Na$_3$(TMPP)$_3$ (175 mg, 0.41 mmol, prepared as in Example 12) was added to 5 mL hexanes. TMEDA (>5 mL) was added to the Na$_3$(TMPP)$_3$ until the solid Na$_3$(TMPP)$_3$ had completely dissolved in the hexanes, indicating complete conversion to Na$_2$(TMPP)$_2$(TMEDA)$_2$. The material need not be isolated, but is prepared in situ during the synthesis of Ti(TMPP)$_2$ below. $^1$H NMR (benzene-d$_6$, 500 MHz, δppm): 1.43 (TMPP, br, 12H, CH$_3$), 1.63 (TMPP, br, 4H, β-CH$_2$), 1.90 (TMEDA, br, 4H, CH$_2$), 1.92 (TMEDA, br, 12H, CH$_3$) 2.13 (TMP, br, 2H, γ-CH$_2$).

13c. Synthesis of bis(2,2,6,6-tetramethylpiperidinato)titanium(II), Ti(TMPP)$_2$ Cold hexanes (10 mL, −35° C.) was added to solid TiCl$_2$(TMEDA)$_2$ (130 mg, 0.37 mmol). The dissolved Na$_2$(TMPP)$_2$(TMEDA)$_2$ was added cold (−35° C.) to the suspension of TiCl$_2$(TMEDA)$_2$ in hexanes. The reaction was allowed to warm to room temperature and stirred for at least 8 hours resulting in a brown solution. The volatiles were removed in vacuum and the resulting oil was dissolved in hexane and filtered through Celite to remove NaCl. The solute was transferred to a round bottom flask and the volatiles were removed in vacuum. The resulting brown oil was lyophilized from benzene to afford a brown solid. Isolated yield: 95 mg (80%). The $^1$H NMR shows shifts assigned to free TMPH ($^1$H NMR (benzene-d$_6$, 500 MHz, δppm): 1.06 (s, 12H, CH$_3$), 1.22 (t, 4H, β-CH$_2$), 1.53 (m, 2H, γ-CH$_2$) and two resonances assigned to TMEDA, which shift depending on concentration (representative $^1$H NMR shifts for TMEDA (benzene-d$_6$, 500 MHz, δppm): 2.04 (br, 12H, CH$_3$), 2.19 (t, 4H, β-CH$_2$)). Electron paramagnetic resonance (EPR) shows an anisotropic signal consistent with an impurity of Ti$_2$Cl$_5$(TMEDA)$_2$ having g-tensor components g$_{xy}$=1.98 and g$_z$=1.93. To evaluate how much of this chlorine-containing impurity was present, a chlorine analysis was carried out as follows: The sample combusted in a flow-through furnace (1100° C.) with platinum catalysis in an atmosphere of oxygen and moisture, and the combustion products in the effluent gas were captured in a trap filled with NaOH and H$_2$O$_2$. After the combustion was complete both the ash and the liquid in the trap were analyzed for chlorine ion. Weight of the sample used: 9.920 mg. Cl in the ash=0.19%; Cl in the effluent gas (liquid in the trap)=2.08%. Based on this chlorine analysis, the amount of the Ti$_2$Cl$_5$(TMEDA)$_2$ impurity is estimated to be only about 6±2 weight % of the product. The Ti(TMP)$_2$ product was purified by sublimation under high vacuum.

The compounds of this invention are useful for the synthesis of materials containing metals. Examples include pure metals, metal alloys, metal oxides, metal nitrides, metal phosphides, metal sulfides, metal borides, metal silicides and metal germanides. Techniques for materials synthesis include vapor deposition (CVD and ALD), liquid solution methods (sol-gel and precipitation) and solid-state pyrolysis.

Vapors useful in vapor deposition can be made by sublimation or distillation from bubblers, or by rapid evaporation of solutions in solvents. The solvents for these solutions must not react with the metal precursors, should have rates of evaporation similar to those of the metal precursors, and have melting points well below room temperature. The compounds of this invention are highly soluble in hydrocarbon solvents, such as alkanes, alkenes or terpenes. Preferred solvents include the saturated hydrocarbons dodecane, tetradecane, 2,6,10-trimethyldodecane (commonly called farnesane), 2,2,4,4,6,8,8-heptamethylnonane (commonly called cyprane), 2,6,10-trimethylpentadecane (commonly called norpristane), and 2,6,10,14-tetramethylpentadecane (commonly called pristane). Another class of suitable solvents includes trialkylamines, such as tri-n-butylamine, tri-n-pentylamine, tri-n-hexylamine, tri-n-heptylamine and tri-n-octylamine.

Those skilled in the art will recognize or be able to ascertain using no more than routine experimentation, many equivalents to the specific embodiments of the invention described specifically herein. Such equivalents are intended to be encompassed within the scope of the following claims.

What is claimed is:
1. A composition comprising
   a compound represented by the formula M$_x$A$_y$ or an oligomer thereof; and
   wherein M is a metal;
   A is a cyclic amine ligand bonded to said M; and
   x and y are positive integers;
   wherein said metal M is selected from the group consisting of manganese, iron, cobalt, nickel, zinc, chromium, vanadium, titanium, magnesium, calcium, strontium, barium, tellurium, cadmium, tin, lead, palladium, platinum, rhodium, ruthenium, osmium, iridium, molybdenum, tungsten, niobium, tantalum, aluminum, gallium, scandium, antimony, indium, lutetium, ytterbium, thulium, erbium, thallium, yttrium, holmium, dysprosium, terbium, gadolinium, europium, samarium, neodymium, praseodymium, cerium, bismuth, and uranium.

2. The composition of claim 1, wherein the compound has the structure

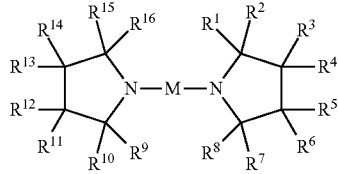

or oligomers thereof, where the $R^1$ through $R^{16}$ are chosen independently from hydrogen, alkyl, substituted alkyl, cycloalkyl, substituted cycloalkyl, aryl, substituted aryl, alkenyl, substituted alkenyl, alkynyl, substituted alkynyl, trialkylsilyl, dialkylamide or haloalkyl groups.

3. The composition of claim 2, wherein the metal is selected from manganese, iron, cobalt, nickel, chromium, vanadium, titanium, magnesium, calcium, strontium, barium, cadmium, zinc, tin, lead, tellurium, europium, palladium, platinum, rhodium, ruthenium, osmium, iridium, molybdenum, tungsten, niobium and tantalum.

4. The composition of claim 1, wherein the cyclic amine ligand comprises 2,2,5,5-tetramethylpyrrolidine.

5. The composition of claim 3, wherein the compound is bis(2,2,5,5-tetramethylpyrrolidin-1-yl)metal(II) represented by the general formula

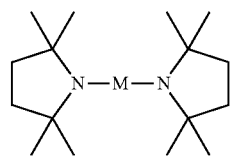

or oligomers thereof, wherein the metal M is selected from the group consisting of manganese, iron, cobalt, nickel, chromium, vanadium, titanium, magnesium, calcium, strontium, barium, cadmium, zinc, tin, lead, tellurium, europium, palladium, platinum, rhodium, ruthenium, osmium, iridium, molybdenum, tungsten, niobium and tantalum.

6. The composition of claim 4, wherein the compound has the chemical name bis(2,2,5,5-tetramethylpyrrolidin-1-yl)manganese(II) dimer and represented by the formula

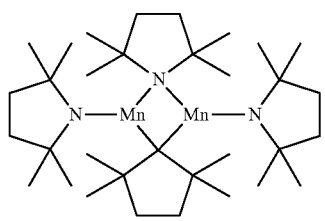

7. The composition of claim 1, wherein the compound has the chemical name bis(2,2,5,5-tetramethylpyrrolidin-1-yl)iron(II) and formula:

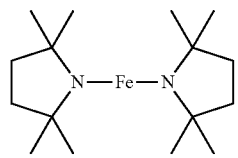

8. The composition of claim 1, wherein the compound has the chemical name bis(2,2,5,5-tetramethylpyrrolidin-1-yl)cobalt(II) and formula

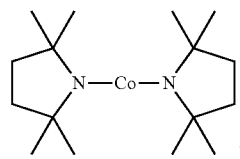

9. The composition of claim 1, wherein the compound has the chemical name bis(2,2,5,5-tetramethylpyrrolidin-1-yl)nickel(II) and formula

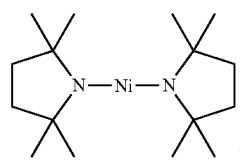

10. The composition of claim 1, wherein the compound has the chemical name bis(2,2,5,5-tetramethylpyrrolidin-1-yl)titanium(II) dimer and formula

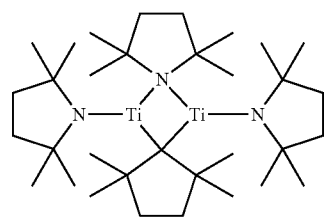

11. The composition of claim 1, wherein the compound has the chemical name bis(2,2,5,5-tetramethylpyrrolidin-1-yl)chromium(II) dimer and formula

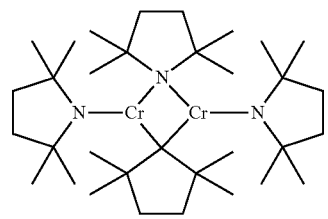

12. The composition of claim 1, wherein the compound is represented by the general formula,

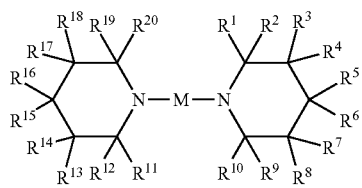

or oligomers thereof where the $R^1$ through $R^{20}$ are chosen independently from hydrogen, alkyl, substituted alkyl, cycloalkyl, substituted cycloalkyl, aryl, substituted aryl, alkenyl, substituted alkenyl, alkynyl, substituted alkynyl, trialkylsilyl, dialkylamide or haloalkyl groups.

13. The composition of claim 12, wherein the metal M is selected from the group consisting of manganese, iron, cobalt, nickel, chromium, vanadium, titanium, calcium, strontium, barium, lead, tellurium, europium, palladium, platinum, rhodium, ruthenium, osmium, iridium, molybdenum, tungsten, niobium and tantalum.

14. The composition of claim 12, wherein the cyclic amine ligand comprises 2,2,6,6-tetramethylpiperidine.

15. The composition of claim 13 wherein the compound is bis(2,2,6,6-tetramethylpiperidin-1-yl)metal(II) represented by the general formula

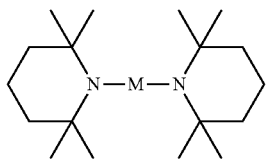

16. The composition of claim 14, wherein the compound has the chemical name bis(2,2,6,6-tetramethylpiperidin-1-yl)manganese(II) and formula

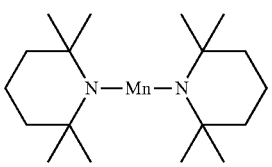

17. The composition of claim 14, wherein the compound has the chemical name bis(2,2,6,6-tetramethylpiperidin-1-yl)cobalt(II) and formula:

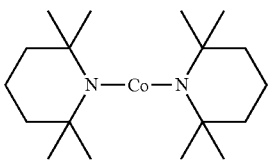

18. The composition of claim 14, wherein the compound has the chemical name bis(2,2,6,6-tetramethylpiperidin-1-yl)nickel(II) and formula:

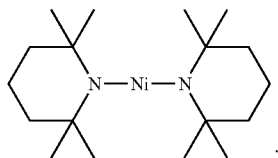

19. The composition of claim 14, wherein the compound has the chemical name bis(2,2,6,6-tetramethylpiperidin-1-yl)titanium(II) and formula:

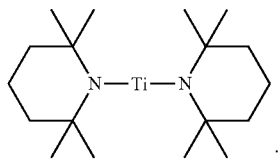

20. The composition of claim 1, wherein the compound is represented by the general formula,

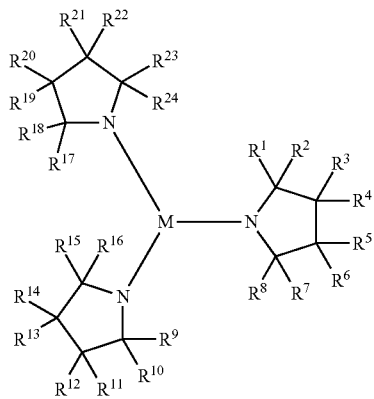

or oligomers thereof where the $R^1$ through $R^{24}$ are chosen independently from hydrogen, alkyl, substituted alkyl, cycloalkyl, substituted cycloalkyl, aryl, substituted aryl, alkenyl, substituted alkenyl, alkynyl, substituted alkynyl, trialkylsilyl, dialkylamide or haloalkyl groups.

21. The composition of claim 20, wherein the metal M is selected from the group consisting of aluminum, cobalt, iron, gallium, vanadium, titanium, rhodium, ruthenium, osmium, iridium, chromium, molybdenum, tungsten, niobium, tantalum, scandium, antimony, indium, lutetium, ytterbium, thulium, erbium, thallium, yttrium, holmium, dysprosium, terbium, gadolinium, europium, samarium, neodymium, praseodymium, cerium, bismuth and uranium.

22. The composition of claim 1, wherein the compound is represented by the general formula,

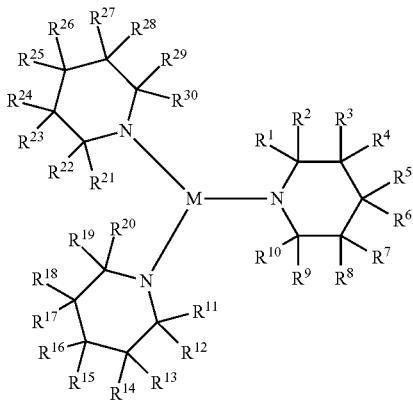

or oligomers thereof where the $R^1$ through $R^{30}$ are chosen independently from hydrogen, alkyl, substituted alkyl, cycloalkyl, substituted cycloalkyl, aryl, substituted aryl, alkenyl, substituted alkenyl, alkynyl, substituted alkynyl, trialkylsilyl, dialkylamide or haloalkyl groups.

23. The composition of claim 22, wherein the metal M is selected from the group consisting of aluminum, cobalt, iron, gallium, vanadium, titanium, rhodium, ruthenium, osmium, iridium, chromium, molybdenum, tungsten, niobium, tantalum, scandium, antimony, indium, lutetium, ytterbium, thulium, erbium, thallium, yttrium, holmium, dysprosium, terbium, gadolinium, europium, samarium, neodymium, praseodymium, cerium, bismuth or uranium.

24. A method comprising:
depositing material from a compound represented by the formula $M_xA_y$ or an oligomer thereof; and
wherein M is a metal;
A is a cyclic amine ligand bonded to said metal M; and
x and y are positive integers;
wherein said metal M is selected from the group consisting of manganese, iron, cobalt, nickel, zinc, chromium, vanadium, titanium, magnesium, calcium, strontium, barium, tellurium, cadmium, tin, lead, palladium, platinum, rhodium, ruthenium, osmium, iridium, molybdenum, tungsten, niobium, tantalum, aluminum, gallium, scandium, antimony, indium, lutetium, ytterbium, thulium, erbium, thallium, yttrium, holmium, dysprosium, terbium, gadolinium, europium, samarium, neodymium, praseodymium, cerium, bismuth, and uranium.

25. The method of claim 24, wherein said depositing includes a second reactant.

26. The method of claim 25, wherein said depositing second reactant is carried out at the same time as said depositing a compound.

27. The method of claim 25, wherein said depositing second reactant and said depositing a compound are carried out at separate times.

28. The method of claim 27, further comprising applying a purge gas between said depositing a compound and said depositing a second reactant.

29. The method of claim 25, wherein said second reactant comprises hydrogen.

30. The method of claim 25, wherein said second reactant comprises ammonia.

31. The method of claim 25, wherein said second reactant comprises water, oxygen, hydrogen peroxide, nitrogen dioxide or ozone.

32. The method of claim 25, wherein said second reactant comprises hydrogen sulfide.

33. The method of claim 25, wherein said second reactant comprises diborane.

34. The method of claim 24, wherein said compound is deposited from a solvent.

35. The method of claim 34, wherein said solvent is a hydrocarbon selected from a group consisting of alkanes, alkenes, terpenes, and combinations thereof.

36. The method of claim 34, wherein said solvent is a saturated hydrocarbon selected from the group consisting dodecane, tetradecane, 2,6,10-trimethyldodecane, 2,2,4,4,6,8,8-heptamethylnonane, 2,6,10-trimethylpentadecane and 2,6,10,14-tetramethylpentadecane and combinations thereof.

37. The method of claim 34, wherein said solvent is a trialkylamine.

38. The method of claim 37, wherein said trialkylamine is selected from the group consisting of tri-n-butylamine, tri-n-pentylamine, tri-n-hexylamine, tri-n-heptylamine, tri-n-octylamine and combinations thereof.

* * * * *